United States Patent [19]

Severino

[11] 4,046,822
[45] Sept. 6, 1977

[54] METHOD FOR RECOVERING ETHYLENE VALUES

[75] Inventor: Frank Titus Severino, Teaneck, N.J.

[73] Assignee: Stauffer Chemical Company, Westport, Conn.

[21] Appl. No.: 417,648

[22] Filed: Nov. 20, 1973

Related U.S. Application Data

[63] Continuation-in-part of Ser. No. 191,975, Oct. 26, 1971, abandoned.

[51] Int. Cl.² ............................................. C07C 17/00
[52] U.S. Cl. .................................. 260/659 A; 260/660
[58] Field of Search ........................... 260/659 A, 660

[56] References Cited

U.S. PATENT DOCUMENTS

| 2,403,977 | 7/1946 | Heard | 260/660 |
|---|---|---|---|
| 3,267,163 | 8/1966 | Tsutsumi et al. | 260/660 |
| 3,488,398 | 1/1970 | Harpring et al. | 260/659 A |
| 3,536,770 | 10/1970 | Skaperdas et al. | 260/659 A |
| 3,799,998 | 3/1974 | Mead | 260/659 A |

FOREIGN PATENT DOCUMENTS

| 1,421,903 | 11/1965 | France | 260/660 |
|---|---|---|---|
| 13,016 | 7/1966 | Japan | 260/660 |
| 1,096,594 | 12/1967 | United Kingdom | 260/660 |
| 733,896 | 7/1955 | United Kingdom | 260/660 |
| 1,225,141 | 3/1971 | United Kingdom | 260/659 A |
| 1,184,576 | 3/1970 | United Kingdom | 260/660 |

Primary Examiner—Delbert E. Gantz
Assistant Examiner—Joseph A. Boska
Attorney, Agent, or Firm—Ellen P. Trevors; Daniel S. Ortiz

[57] ABSTRACT

An improved ethylene oxychlorination process wherein the unreacted ethylene in the process off-gas is dried and reacted with chlorine in the presence of a non-reactive liquid to form ethylene dichloride, (1,2-dichloroethane) recovering the ethylene dichloride. The improved process includes a method for drying the gas by contact with ethylene dichloride.

6 Claims, 5 Drawing Figures

METHOD FOR RECOVERING ETHYLENE VALUES

CROSS REFERENCE TO RELATED APPLICATION

This application is a continuation-in-part of U.S. Ser. No. 191,975, filed Oct. 26, 1971 now abandoned.

BACKGROUND OF THE INVENTION

Processes to prepare chlorinated hydrocarbons by the reaction of ethylene, hydrogen chloride and an oxygen-containing gas in the presence of a deacon catalyst are well known and are known in the art as oxychlorination processes. Oxychlorination processes can be carried out in fixed beds as disclosed in British Pat. No. 1,104,666 or in fluid beds as disclosed in British Pat. No. 937,985.

The commercial processes usually provide a reaction mixture containing an excess of ethylene and oxygen to insure maximum conversion of hydrogen chloride to chlorinated hydrocarbon. Maximum conversion of hydrogen chloride is desirable since any unconverted hydrogen chloride is separated from the chlorinated hydrocarbons with the water formed in the reaction. The hydrogen chloride is difficult to recover from the water phase and is usually lost as a waste product from the process. In order to insure maximum utilization of the hydrogen chloride, the ethylene and oxygen are usually provided in excess of that stoichiometrically required to react the hydrogen chloride to the desired chlorinated hydrocarbons. Processes which do not provide an excess of ethylene over that requires to react with the hydrogen chloride usually have sufficient unreacted ethylene in the process off-gas to make the recovery of the unreacted ethylene values economically desirable. The unreacted gases which remain after condensation of the water and the chlorinated hydrocarbons formed in the oxychlorination reaction usually contain oxygen, nitroge, water, small amounts of hydrogen chloride, uncondensed chlorinated hydrocarbons and from about 0.05 to about 25% ethylene. After separating the chlorinated hydrocarbons, water, and hydrogen chloride, the process off-gases can be vented to the atmosphere which adds to atmospheric pollution or burned. The discarding of the ethylene values in the off-gas can present a serious economic loss of ethylene oxychlorination processes.

Processes for recovering the ethylene values from the oxychlorination process off-gas have been developed. Processes such as that disclosed in French Pat. No. 1,421,903 react the ethylene in the wet oxychlorination process off-gas with chlorine, in the vapor phase, at an elevated temperature, in the presence of an iron catalyst, to chlorinate the ethylene in the process off-gas to ethylene dichloride and recover the chlorinated hydroncarbons from the inert and unreacted gases. As used herein ethylene dichloride is used to refer to 1,2-dichloroethane.

Processes of the type which react the ethylene in the wet oxychlorination process off-gas in the vapor phase with chlorine in the presence of a catalyst have two major disadvantages. The processes utilize the gas phase containing relatively large amounts of water vapor. The reaction of ethylene and chlorine in the vapor phase in the presence of a catalyst at an elevated temperature is not selective to ethylene dichloride. Oxygen containing compounds are formed which must be separated from the ethylene dichloride product and can add to the water pollution problems which the process presents. The by-products represent a considerable loss of recoverable ethylene values. Since a substantial amount of water is present during the chlorination, corrosion resistant equipment must be utilized to combat the combined action of water and chlorine. The use of corrosion resistant process equipment presents a significant cost factor in determining the economic feasibility of recovering the ethylene values from ethylene oxychlorination process off-gas.

It is the object of the present invention to provide an improved process for producing ethylene dichloride by the oxychlorination of ethylene. It is an object of the present invention to provide a process in which ethylene values can be economically recovered from oxychlorination process off-gas. It is a further object of the present invention to provide a process which can be accomplished without the need for process equipment fabricated of expensive corrosion resistant materials. It is another object of the present invention to provide a process which is selective to production of ethylene dichloride from ethylene and chlorine and which minimizes the production of oxygenated compounds. It is still a further object of the present invention to provide an improved process which reduces the air pollution potential of ethylene oxychlorination process.

BRIEF DESCRIPTION OF THE INVENTION

In accordance with the present invention in a process wherein ethylene dichloride is produced by reaction of ethylene, hydrogen chloride and an oxygen containing gas in the presence of an oxychlorination catalyst and where ethylene is present in the process off-gas after separation of the ethylene dichloride product and water of reaction, the improvement which comprises recovering unreacted ethylene values from the product off-gas by drying the process off-gas, reacting the ethylene values in the process off-gas with chlorine in the presence of a non-reactive liquid to form ethylene dichloride and recovering the ethylene dichloride. The process is particularly useful when ethylene dichloride leaving the sytem is used as a desiccant.

Detailed Description of the Invention

The oxychlorination processes which are useful in combination with the present invention are well known in the art. They are processes in which hydrogen chloride, oxygen and ethylene are contacted at an elevated temperature in the presence of an oxychlorination or deacon catalyst to form chlorinated hydrocarbons and most advantageously ethylene dichloride. Ethylene oxychlorination processes of this type usually operate at pressures of from about 2 to about 20 atmospheres. The oxychlorination reaction temperature is usually controlled in the range of about 220° to about 380° C. The reaction occurs in the presence of an oxychlorination catalyst in a static (fixed) or a fluid bed.

After the oxychlorination reaction, the reaction mixture is usually cooled to condense the water and the chlorinated hydrocarbons formed in the reaction and leave an oxychlorination process off-gas which contains ethylene, inert gaseous materials, water and chlorinated hydrocarbon. The process off-gases can be vented to the atmosphere and the ethylene values and residual chlorinated hydrocarbon wasted.

Figure 1:
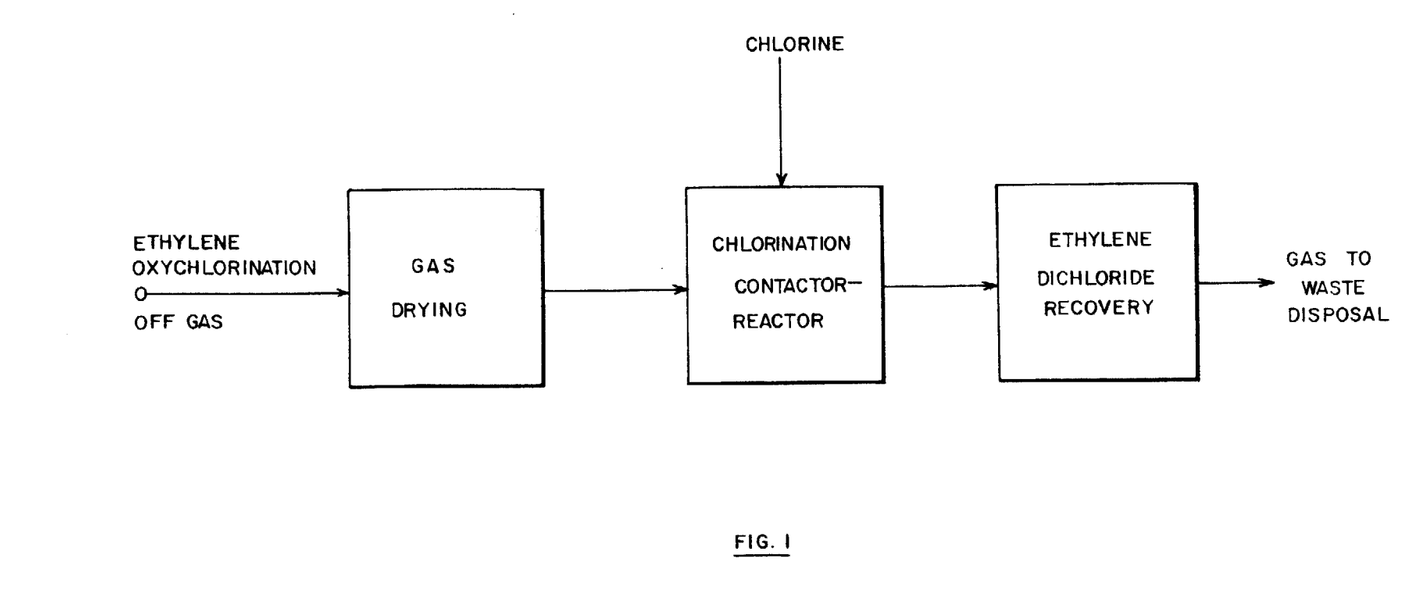
FIG. 1 is a diagrammatic representation of the process.

FIG. 1 is a diagrammatic representation of the process of the present invention. The oxychlorination off-gas is first dried, then reacted with chlorine in the presence of a non-reactive liquid and the chlorinated hydrocarbons recovered.

In the process of the present invention the oxychlorination process off-gas is first dried. The oxychlorination process off-gas gases can be dried by contacting the gas with known drying agents such as sulfuric acid, calcium chloride, molecular sieves, anhydrous aluminum chloride, activated alumina or the like, of the process off-gases can be cooled to temperatures in the range of about 5° C. to about −35° C. and the condensate separated from the gaseous material. If the temperature is sufficiently low and the pressure relatively high, the water content of the oxychlorination process off-gas can be reduced to levels sufficiently low that the gases can be utilized in the process of the present invention without further treatment. The method for drying the oxychlorination process off-gases is determined by the pressure and the temperature to which the oxychlorination process off-gases can be lowered by the use of cooling water and available outlets for by-product drying agents such as spent sulfuric acid. In order to minimize the use of chemical reagents, the preferred method for drying the oxychlorination process off-gases comprises cooling the gases to the range of about 5° to about −35° C., separating the condensate from the gaseous material and contacting the gaseous material with a drying agent such as ethylene dichloride anhydrous calcium chloride, anhydrous aluminum chloride or molecular sieves. The use of ethylene dichloride as the disiccant is preferred. This method of drying the oxychlorination process off-gas can provide a gas containing less than about 25 parts per million (weight basis) water with a minimum utilization of chemical reagents. The two step drying of the oxychlorination process off-gas is advantageous in that a back-up system is provided should any liquid carry over from the refrigeration drying system. It is critical that the water content of the oxychlorination off-gas be reduced to a level such that the water content of the liquid phase in the subsequent contactor-reactor is maintained below about 50 parts per million and preferably lower than about 45 parts per million and most preferably, below about 35 parts per million (weight basis).

The dried oxychlorination process off-gases containing major portions of inerts, from about 0.1 to about 25% ethylene, chlorinated hydrocarbons and minor amounts of hydrogen chloride and very small amounts of water vapor are then passed to the chlorinator. The chlorinator is an apparatus wherein dried oxychlorination process off-gas containing ethylene is contacted with chlorine in the presence of a non-reactive solvent which is preferably 1,2-dichloroethane. The solvent contains catalytic amounts of a matarial such as ferric chloride to increase the rate of reaction between the ethylene and chlorine. Iron chloride is the preferred catalytic material and is usually present in concentrations of between about 1 to about 40 parts per million (weight basis) in the liquid materials. The ferric chloride is not added to the circulating liquid but is picked up by contact with the mild steel equipment. Chlorine is generally provided in about an equimolar ratio to the ethylene which is reacted from the off-gas stream but amounts less than stoichiometric to a slight excess can be tolerated. Any type of contactor-reactor suitable for contacting gaseous and liquid materials can be utilized in the process of the present invention. It is preferred however to utilize a mild steel column packed with steel raschig rings over which ethylene dichloride is circulated. The dry ethylene oxychlorination off-gas can be cocurrently or counter-currently contacted with the chlorine in the presence of the non-reactive liquid. The chlorine which is soluble in solvents such as ethylene dichloride is dissolved in the liquid phase. The ethylene is absorbed from the gas phase by the liquid and rapidly reacts with the chlorine to form ethylene dichloride. Ethylene dichloride is preferred liquid since it is non-reactive, a good solvent for chlorine, and a product of the reaction. Although ethylene dichloride is the preferred non-reactive liquid, other liquids which are non-reactive solvents for chlorine and ethylene dichloride and have a boiling point above ethylene dichloride can be utilized. The heat of reaction can be removed from the circulating ethylene dichloride stream by heat exchange means. The temperature of the circulating ethylene dichloride is adjusted so that the temperature is maintained between about 35° and about 80° C. and preferably between about 40° and about 60° C.

The oxychlorination process off-gas which has been contacted with chlorine in the contactor-reactor is substantially saturated with ethylene dichloride or other non-reactive solvent at the temperature and pressure of the gas stream and can contain a small amount of chlorine which has been stripped from the circulating liquid by the inert gases or has not been asborbed in the circulating liquid. The gas mixture from the contactor-reactor can be contacted with additional liquid to insure that no chlorine leaves the process and the gas passed to a means for separating the ethylene dichloride in the vapor from the unreacted and inert gases.

The gas mixture containing ethylene dichloride is then further processes to recover the ethylene dichloride. The gas mixture containing ethylene dichloride can be cooled and refrigerated to temperatures as low as about −35° C. to recover a major portion of the ethylene dichloride. At pressures in the range of 2 to about 10 atmospheres, temperatures in the range of 0° to about −35° C. are suitable. When the pressure at which the process is operated is relatively high, and the temperature to which the gas mixture is refrigerated is low, a substantial portion of the chlorinated hydrocarbons in the inert gases can be condensed from the inert and unreacted gases and separated and where pollution laws are not strict, the gaseous mixture can be vented to the atmosphere.

The concentration of chlorinated hydrocarbons in the gases vented to the atmosphere can be reduced to levels below about 100 parts per million if required by contacting the inert gases containing chlorinated hydrocarbons with a high boiling point hydrocarbon solvent in which the chlorinated hydrocarbons are soluble. A normal nine carbon hydrocarbon solvent is a suitable absorbent but mixtures of aromatic hydrocarbons and alkane hydrocarbons boiling within a range of from about 90° C. to about 200° C. can be used. The chlorinated hydrocarbon are absorbed in the solvent and the inert gases can be vented to the atmosphere. This method can produce a vent gas containing only small quantities of unreacted ethylene and low levels of chlorinated hydrocarbons.

The ethylene dichloride can be stripped or distilled from the high boiling point inert hydrocarbon solvent and the hydrocarbon solvent cooled, and recirculated to absorb additonal ethylene dichloride from the gas stream.

The operation of the process for recovering ethylene values from the oxychlorination process off-gases is aided by operation at elevated pressures. Elevated pressures aid in condensing the water vapor and chlorinated hydrocarbons from the gas streams and in absorption of the ethylene and chlorine in the contactor-reactor system. Pressures from about 1 to about 20 atmospheres are satisfactory and the process is preferably operated at pressures in the range of about 3 to about 10 atmospheres.

Figure 2:
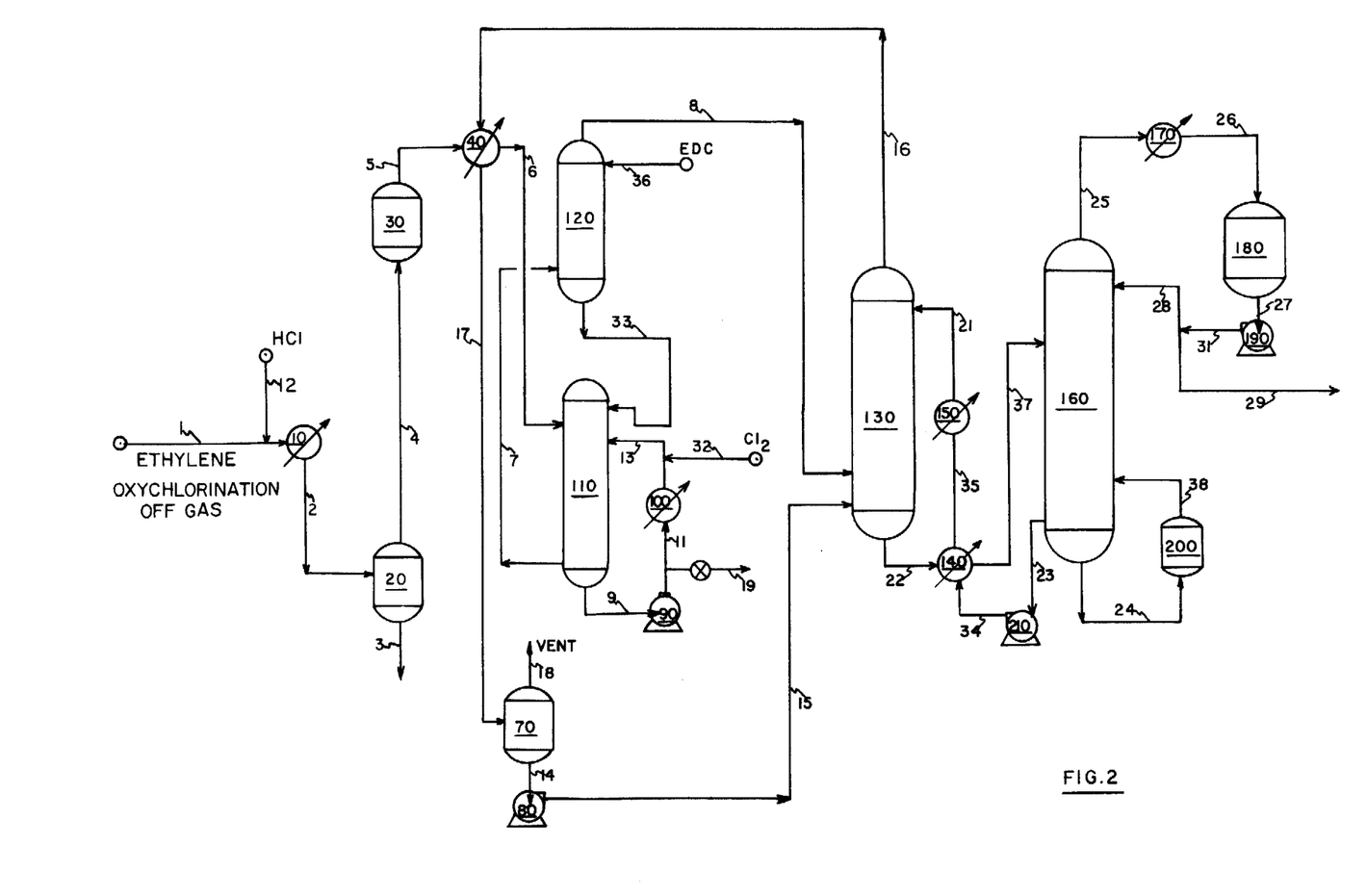
FIG. 2 is a diagrammatic representation of the process wherein the chlorinated hydrocarbons are recovered from the gas stream by absorption.

A preferred embodiment of the present invention is illustrated in FIG. 2. The off-gas from the ethylene oxychlorination process is obtained from the oxychlorination zone through line 1 at a temperature between about 5° and about 60° C. and at a pressure from about 1 to about 20 atmospheres. The off-gas is passed to heat exchanger 10 wherein the temperature is reduced to from about 5° to about −35° C. If the oxychlorination off-gas does not contain sufficient hydrogen chloride to prevent icing of the heat exchanger, additional hydrogen chloride can be added through line 12 to prevent freezing in the cold heat exchanger 10.

The chilled oxychlorination process off-gas is then passes to gas-liquid separator 20 which can be an empty separator vessel or contain mist elimination means to sepatate the condensed liquid from the gaseous phase. The condensate which consists mainly of ethyl chloride, ethylene dichloride, water and small amounts of hydrogen chloride which may have been admitted to the system to control icing are removed through line 3.

The cold gaseous mixture is passed through line 4, to gas dryer 30 which can be a vessel which contains a bed of dessicant material such as anhydrous calcium chloride, molecular sieves, activated aluminia or the like or a column irrigated with sulfuric acid or ethylene dichloride. The substantially anhydrous gas mixture containing inert gases, ethylene and a small amount of of chlorinated hydrocarbons is then passed through line 5 to heat exchanger 40 where the gas stream is warmed by heat exchange with the vent gases from column 130.

The gas mixture is dried so that it can be handled and reacted with chlorine in the liquid phase without the need for corrosion resistant process equipment made from carbon or expensive metals or alloys. After the drying zone, process equipment can be fabricated from steel which is suitable for use under the temperature and pressure conditions in the process.

The warm gases then proceed through line 6 to the contactor-reactor column 110. Column 110 is a tower packed with iron raschig rings over which ethylene dichloride is circulated through line 9, pump 90, line 11, heat exchanger 100 and line 13. Heat exchanger 100 is utilized to control the temperature of the circulating liquid by removing the heat of the chlorination reaction.

The temperature is controlled in the range of about 35° to about 85° C. and preferably in the range of 40° to 60° C. Chlorine can be added to line 13 through line 32, or can be added directly to the column. The dried ethylene oxychlorination process off-gas entering column 110 through line 6 is cocurrently contacted with the circulating ethylene dichloride and chlorine. The ethylene is dissolved in the liquid phase, is reacted with the chlorine, and is removed from the column as ethylene dichloride product. The circulation through heat exchanger 100 is controlled to effectively wet the tower packing so that the ethylene and chlorine are effectively contacted and reacted to provide a medium to control the reactor temperature. The level in column 110 is controlled by withdrawal of circulating liquid from line 11 through line 19. The material from line 19 can be mingled with ethylene dichloride streams from other parts of the process.

The amount of chlorine which enters column 110 is generally controlled in response to monitoring the amount of chlorine in the liquid in line 9 and the amount of ethylene in the vent gases in line 18.

The gaseous mixture having a substantial portion of the ethylene removed and reacted in column 110 is then passed through line 7 to column 120. Column 120 is a packed column which is irrigated by ethylene dichloride entering the column through line 36. The gas mixture from column 110 is contacted with the ethylene dichloride to insure that the gas mixture in line 8 is substantially free of chlorine. The underflow from column 120 passes through line 33 to column 110 where it is utilized to contact the gas mixture containing ethylene. Columns 110 and 120 can be combined into one column when countercurrent contacting is desired. Column 110 can be operated with countercurrent flow of ethylene containing gas and liquid.

The oxychlorination process off-gases having a substantial portion of the ethylene reacted to ethylene dichloride then proceeds through line 8, to absorption column 130. The gas mixture leaving column 120 has substantially all of the ethylene reacted to ethylene dichloride but contains a considerable amount of ethylene dichloride in the vapor phase since the gas mixture has contacted a stream of warm ethylene dichloride.

Column 130 is an absorption column wherein the gas mixture containing ethylene dichloride is contacted with an inert hydrocarbon solvent which absorbs the ethylene dichloride from the gas stream. Absorption column 130 can be a packed column tray column design. The gas leaving column 130 having the major portion of the chlorinated hydrocarbons removed, passes through line 16 and is cooled by interchange with the cold gases from dryer 30. Any chlorinated hydrocarbons or hydrocarbon solvent which condenses is separated from the gas stream in separator 70 and the gases are passed to the vent system through line 18. The vent line has pressure control means to maintain pressure on the system. Any liquid separated from the gas stream in separator 70 is returned to column 130 through line 14, pump 80 and line 15.

The hydrocarbon solvent which has absorbed the ethylene dichloride from the gaseous stream is passed through line 22 to heat exchanger 140 where it is heated by exchange of heat with stripped solvent from the column 160 and enters stripping column 160 through line 37. Column 160 can be a tray or packed column design in which the ethylene dichloride rich hydrocarbon solvent enters at some point below the top of the column and is passed downwardly through the column countercurrent to a flow of vaporized ethylene dichloride which is provided by circulation of the column bottoms through line 24 and heat exchanger reboiler 200. The ethylene dichloride passes out of column 160 through line 25, is condensed in condenser 170 and flows through line 26 to reflux accumulator 180. The reflux flows through line 27 to pump 190. The ethylene dichloride is pumped through line 31. A portion of the ethylene dichloride is returned to column 160 as reflux through line 28 and the ethylene dichloride product is removed from the process through line 29. The stripped solvent is passed through line 23 to pump 210 and is pumped through line 34 to heat exchanger 140 where the stripped solvent is cooled by heat exchange with ethylene dichloride rich solvent from column 130 and passes through line 35 to water cooled heat exchanger 150 and through line 21 to column 130. The ethylene dichloride from line 19 and line 29 is dry and can be passed to the storage for dry ethylene dichloride or mixed with the wet material from vessel 20 in line 3 and treated as wet crude ethylene dichloride.

The absorption column can be operated at temperatures up to about 90° C. depending upon the absorbent chosen, the size of the absorbing column and the pressure in the absorber. Generally high pressures and low temperatures favor effective absorption of the ethylene dichloride.

The stripper (Col. 160) is usually operated under relatively low pressures to aid in separating the ethylene dichloride from the absorbent at moderate temperatures. The pressure and temperature of operation is dependent on the solvent but is usually from about atmospheric to about 3 atmosphere pressure and from about 95° to about 250° C.

Figure 3:
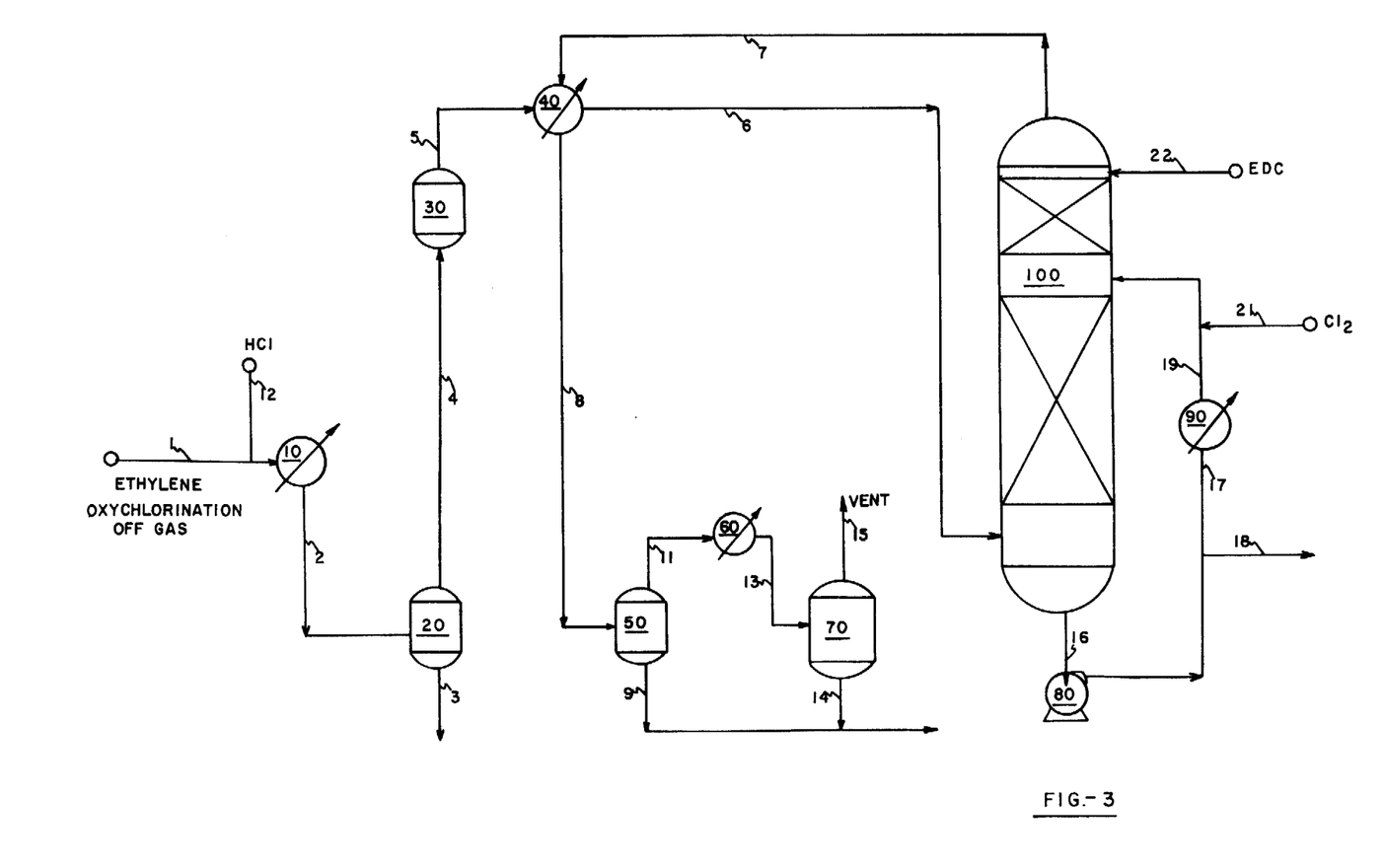
FIG. 3 is a diagrammatic representation of the process wherein the chlorinated hydrocarbons are recovered from the gas stream by condensation.

Another embodiment of the invention is illustrated in FIG. 3.

Oxychlorination off-gas after having the chlorinated hydrocarbons, water, and hydrogen chloride condensed from the system enters the ethylene recovery process through line 1. The ethylene oxychlorination off-gas is usually at an elevated pressure and at a temperature between about 10° and about 60° C. The gas in line 1 enters heat exchanger 10 where the temperature is lowered to the range of about 5° to about −35° C. A major portion of the water and remaining chlorinated hydrocarbons are condensed from the gas stream. The gas and condensed liquid flows through line 2 to gas-liquid separator 20 where the condensed liquid is separated from the gas stream and is removed from the process through line 3. The cooled gas then proceeds through line 4 to dryer 30. The remaining traces of water are removed so that the gas leaving dryer 30 contains less than about 25 parts per million water. The cooled gas is passed through line 5 to heat exchanger 40 where it is warmed by heat exchange with the warm gases from contactor-reactor column 100. The warm dry gas is passed through line 6 to the bottom of contactor-reactor column 100. Contactor-reactor column 100 contains two beds packed with iron raschig rings. The lower bed is irrigated by a circulating stream of ethylene dichloride which is pumped from the bottom of column 100 through line 16 by pump 80. The circulating ethylene dichloride then passes through line 17 to heat exchanger 90 where the circulating stream is cooled, then through line 19 to the top of the lower section of packing in contactor-reactor 100. Chlorine is fed directly into the circulating stream of ethylene dichloride through line 21, but can be admitted directly into column 100. The level in the bottom of contactor-reactor column 100 is controlled by removal of material through line 18. The ethylene dichloride removed through line 18 can contain a small amount of chloride. The ethylene dichloride from line 18 can be contacted with dilute caustic and then dried. The dried oxychlorination off-gas passes counter-currently to the circulating flow of ethylene dichloride and chlorine. The ethylene is absorbed from the gas stream into the ethylene dichloride and is reacted with the chlorine to ethylene dichloride. The ethylene oxychlorination off-gas is then passed to the upper packed section in contactor-reactor 100 where the gas is passed countercurrent to a flow of ethylene dichloride which enters the column through line 22. The upper column section is utilized to insure that chlorine which may be stripped from the circulating ethylene dichloride in the lower section is absorbed from the vent stream so that the gas leaving the system is relatively chlorine-free. The ethylene oxychlorination off-gas having substantially all the ethylene reacted with chlorine contains substantial amounts of ethylene dichloride in the vapor phase. The gas mixture is passed from contactor-reactor column 100 through line 7 to heat exchanger 40 where it is cooled by heat exchange with the cold gases from the drying system and is passed through line 8 to gas-liquid separator 50 where any liquid ethylene dichloride or other liquid chlorinated hydrocarbons which have condensed by cooling in heat exchanger 40 are separated from the gaseous material. The liquid condensate is removed through line 9. The cooled vent gas then passes through line 11 to heat exchanger 60 where the vent gases are further cooled to temperatures as low as about −35° C. and passed through line 13 to gas-liquid separator 70 where the liquid condensed by cooling in heat exchanger 60 is separated from the gaseous material. The cooled gas then passes through line 15 to the vent which is pressure controlled to maintain the desired back pressure on the system. The liquid condensate passes through line 14 to line 9 and then to crude ethylene dichloride storage facilities. The ethylene dichloride which enters the contactor-reactor column 100 through line 22 can be ethylene dichloride from other steps of an integrated process.

The vent gas leaving the system through line 15 is saturated with chlorinated hydrocarbons at the pressure and temperature to which they are cooled in heat exchanger 60. The pressure under which the system is operated and the temperature to which the vent gases are cooled in heat exchanger 60 determines the amount of chlorinated hydrocarbons which are lost in the vent system.

Figure 4:
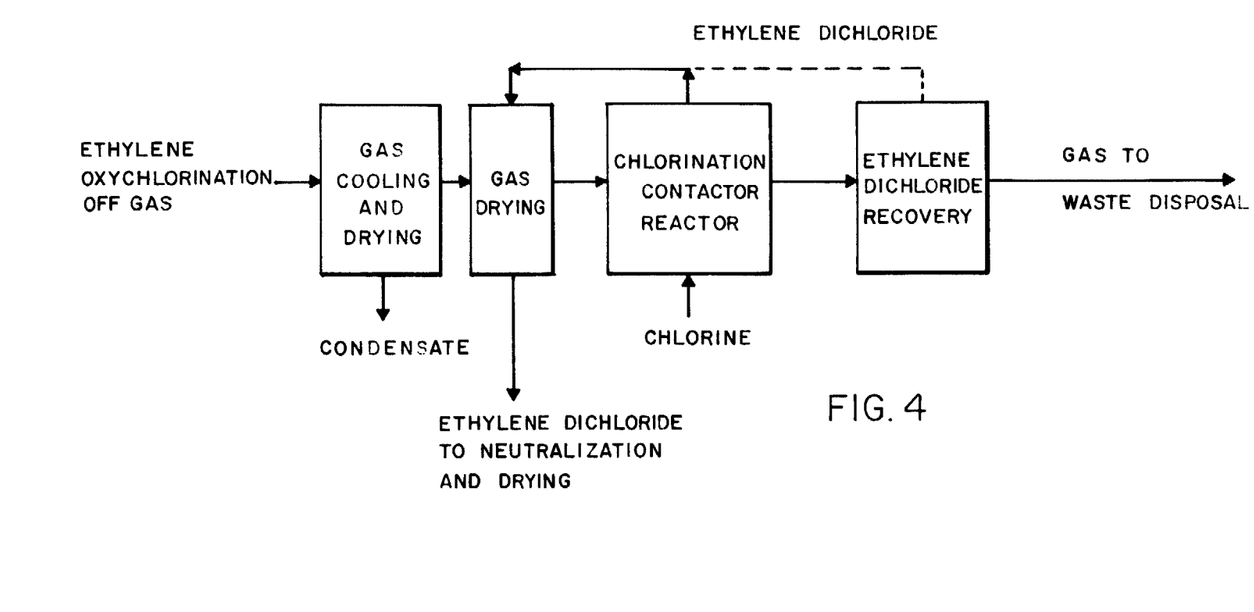
FIG. 4 is a diagrammatic representation of the process wherein ethylene dichloride is utilized as a desiccant.

FIG. 4 is a diagrammatic representation of the process of the present invention wherein the desiccating agent is ethylene dichloride. The ethylene oxychlorination off-gas is first cooled, the condensate is separated from the gas stream and the gas stream which is partially dried is further dried by contact with ethylene dichloride.

FIG. 4 illustrates the use of ethylene dichloride from the contactor-reactor zone or alternatively the ethylene dichloride recovery zone as the drying agent, but dry ethylene dichloride from other sources can be utilized.

In the process illustrated in FIG. 4, the ethylene oxychlorination off-gas is cooled at a temperature between about 5° and about −35° C. to form a liquid phase containing water or dilute hydrogen chloride and condensed chlorinated hydrocarbons. The condensate is separated from the gas stream and the gas stream which contains the equilibrium concentration of water, at the temperature and pressure at which the condensation takes place, is passed to a drying zone where the gas is contacted with ethylene dichloride. Ethylene dichloride must be furnished in an amount sufficient to reduce the water content of the gas stream to an acceptable level. That is, a level such that the water content of the liquid chlorination contactor-reactor is maintained below about 50 parts per million.

The ethylene dichloride is preferably the ethylene dichloride from the chlorination contactor-reactor or the ethylene dichloride recovery zone. However, any source of dry ethylene dichloride is suitable. The ethylene dichloride which has contacted the wet gas is then passed to a ethylene dichloride neutralization and drying zone.

The dry gas containing ethylene, some ethylene dichloride and other inert materials is then passed to the chlorination contactor-reactor where the ethylene is contacted with chlorine in the presence of an inert solvent to form ethylene dichloride. The gas stream is then passed to an ethylene dichloride recovery zone where ethylene dichloride is recovered from the gas stream and the gas stream consisting essentially of inert materials is passed to the atmosphere. The use of the ethylene dichloride as a desiccant reduces the consumption of chemical reagents in the process, provides a process which can be operated under economical conditions to substantially eliminate ethylene from the vent gas.

Figure 5:
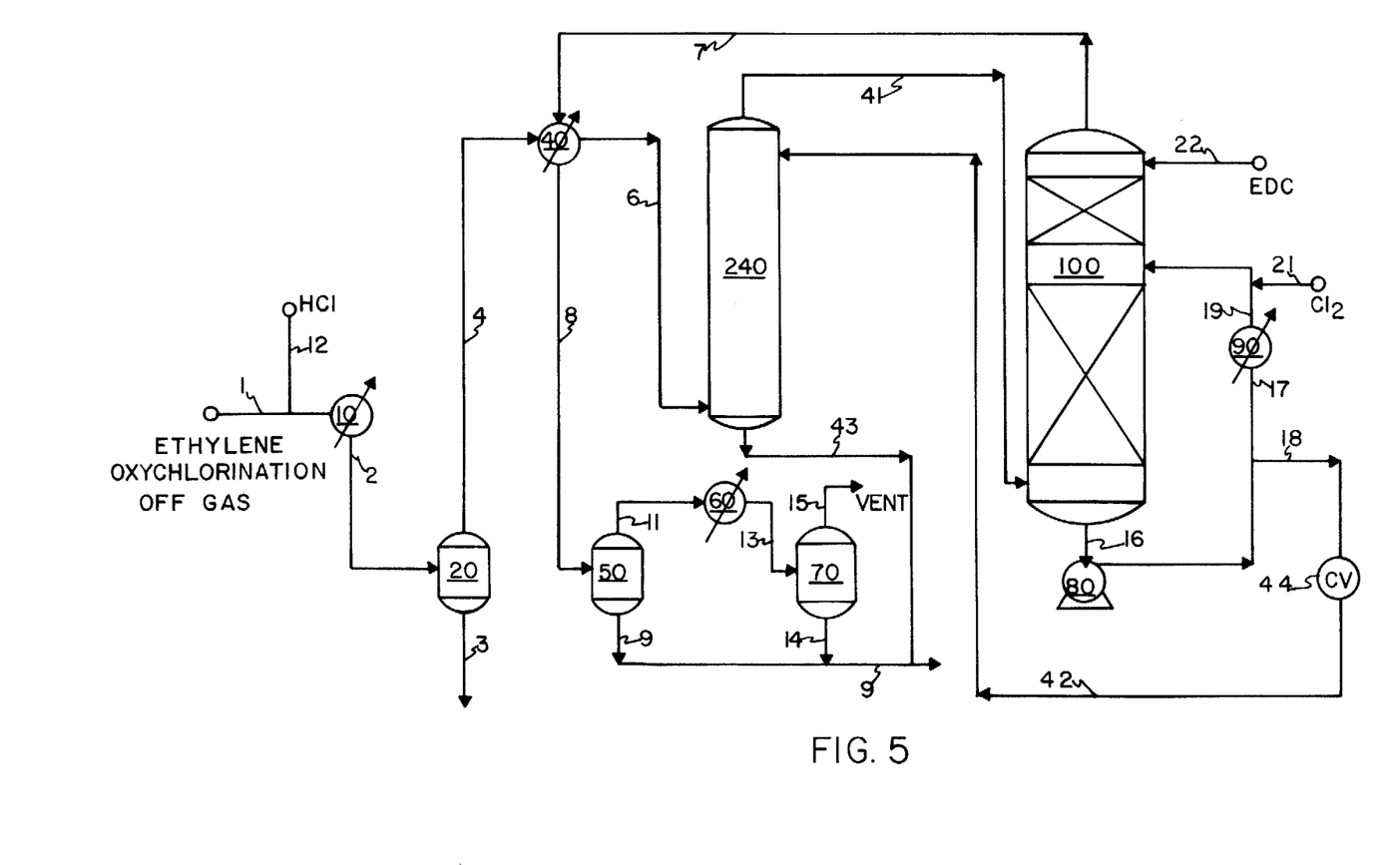
FIG. 5 is a diagrammatic representation of the process illustrated in FIG. 3 with ethylene dichloride utilized as a desiccant.

FIG. 5 illustrates an embodiment of the process as illustrated in FIG. 3 utilizing ethylene dichloride as the desiccating agent. Ethylene oxychlorination off-gas after having the chlorinated hydrocarbons, water, and hydrogen chloride condensed from the reaction mixture enters the ethylene recovery process through line 1. The ethylene oxychlorination off-gas is usually at an elevated pressure and at a temperature between about 10° C. and about 50° C. The gas in line 1 enters heat exchanger 10 where the temperature is lowered to the range of 5° to about −35° C. Hydrogen chloride can be mixed with the gas stream through line 12 to prevent the condensate from freezing in exchanger 10. The water and chlorinated hydrocarbons are condensed from a gas stream at the low temperature. The gas and condensed liquid flow through line 2 to gas liquid separator 20 where the condensed liquid is separated from a gas stream and removed from process through line 3.

The cooled gas passes through line 4 to heat exchanger 40 where it is warmed by heat exchange with the warm gases from the contactor-reactor column 100. The gas passes through line 6 to the bottom of drying column 240. Drying column 240 is packed with raschig rings. The packed column is irrigated by a stream of ethylene dichloride which is pumped from the bottom of column 100. The gas passes through column 240 countercurrent to the flow of ethylene dichloride and leaves column 240 through line 41 and enters the bottom of contactor-reactor column 100.

The ethylene dichloride entering column 240 is passed from circulating line 17 through line 18 and control valve 44 which maintains a level of ethylene dichloride in the bottom of column 100. The ethylene dichloride proceeds through line 42 and enters the top of drying column 240. The ethylene dichloride which has contacted and dried the ethylene oxychlorination off-gas passes through line 43 to line 9 and mixes with the ethylene dichloride from the final condensation system and can pass to a neutralizing and drying zone.

Contactor-reactor column 100 contains two beds packed with iron raschig rings. The lower bed is irrigated by a circulating stream of ethylene dichloride which is pumped from the bottom of column 100 through line 16 by pump 80. The circulating ethylene dichloride then passes through line 17 to heat exchanger 90 where the circulating stream is cooled then through line 19 to the top of the lower section of packing in contactor-reactor 100. Chlorine is fed directly into the circulating stream of ethylene dichloride through line 21, but can be admitted directly into column 100. The level on the bottom of the contactor-reactor column 100 is controlled by removing material through line 18. The ethylene dichloride removed through line 18 can contain a small amount of chlorine. The ethylene dichloride from line 18 is then passed through control valve 44 and line 42 to drying column 240. The dried oxychlorination off-gas passes countercurrently to circulating flow of ethylene dichloride and chlorine. The ethylene is absorbed from the gas stream into the ethylene dichloride and is reacted with the chlorine to ethylene dichloride.

The ethylene oxychlorination off-gas is then passed to the upper packed section in contactor-reactor 100 where the gas is passed countercurrent to a flow of ethylene dichloride which enters the column through line 22. The upper column section is utilized to insure that chlorine which may be stripped from the circulating ethylene dichloride in the lower section is absorbed from the vent stream so that the gas leaving the system is relatively chlorine-free.

The ethylene oxychlorination which has substantially all the ethylene content reacted with chlorine contains substantial amounts of ethylene dichloride in the vapor phase. The gas mixture is passed from contactor-reactor column 100 through line 7 to heat exchanger 40 where it is cooled by heat exchange with the cold gas from the drying system. The cooled mixture is passed through line 8 to gas liquid separator 50 where the liquid ethylene dichloride or other liquid chlorinated hydrocarbons which have condensed by cooling in heat exchanger 40 are separated from the gaseous material. The liquid condensate is removed through line 9.

The cooled vent gas passes through line 11 to heat exchanger 60 where the gases are further cooled to temperatures as low as about −35° C. The gas stream passes through line 13 to gas liquid separator 70 where the liquid condensed by cooling in heat exchanger 60 is separated from the gaseous material. The cooled gas then passes through line 15 to the vent which is pressure controlled to maintain the desired back pressure on the system. The liquid condensate passes through line 14 to line 9 and then to crude ethylene dichloride storage facilities.

The ethylene dichloride which enters the contactor-reactor column 100 through line 22 can be ethylene dichloride from other steps of an integrated process. The vent gas leaving the system through line 15 is saturated with chlorinated hydrocarbons at the pressure and temperature to which they are cooled in heat exchanger 60. The pressure under which this system is operated and the temperatures at which the vent gases are cooled in heat exchanger 60 determines the amount of chlorinated hydrocarbons which are lost in the vent systems.

It is obvious that although high pressure operation is not critical the economics of the process favor operation at elevated pressures so that water and chlorinated hydrocarbons may be removed from the gas stream at relatively high temperature levels. In addition, the high pressure improves the absorption of the ethylene into the liquid ethylene dichloride circulating in contactor-reactor column 100 and provides for utilization of smaller reaction equipment for accomplishing the process.

The process of the present invention will be illustrated by reference to the following illustrative embodiments.

EXAMPLE 1

The process illustrated in FIG. 2 is employed in Example 1. A gaseous stream of oxychlorination process off-gas containing:

2,380 pounds per hour ethylene
1,730 pounds per hour $O_2$
46,500 pounds per hour $N_2$
430 pounds per hour $H_2O$
500 pounds per hour ethyl chloride
6,900 pounds per hour EDC The gaseous stream enters the process through line 1 at a temperature of 40° C. and at 60 psig. pressure. To the gaseous mixture in line 1 is added 70 lbs/hour of hydrogen chloride through line 12. The mixture passes to heat exchanger 10 where the off-gas is cooled to −25° C. The liquid which condenses from the gas stream at −25° C. is separated from the gas in gas-liquid separator 20 and the condensate removed through line 3. The liquid removed in line 3 contains:

250 pounds per hour ethyl chloride
6,700 pounds per hour ethylene dichloride
424 pounds per hour water
70 pounds per hour hydrogen chloride The gas stream leaves gas-liquid separator 20 through line 4 and contains:

1,730 pounds per hour $O_2$
46,500 pounds per hour nitrogen
200 pounds per hour ethylene dichloride
250 pounds per hour ethyl chloride
6 pounds per hour water The gas stream enters dryer 30 which contains a 4 feet, 6 inch diameter by 9 feet bed of anhydrous calcium chloride in pellet form. The gas leaves the dryer at about −25° C. and passes through heat exchanger 40 where it is warmed to 25° C. by interchange with the heat from the gas stream from absorber column 130. The gas stream in line 6 contains less than 30 parts per million by weight of water. The gas is passed through column 110 cocurrent to the flow of circulating ethylene dichloride. Column 110 is a 10 feet, 6 inch diameter by 15 feet column with a 10 foot packed bed of 1 inch carbon steel raschig rings. The column is irrigated by the circulation of 530,000 pounds per hour of ethylene dichloride circulating through line 9, pump 90, line 11, heat exchanger 100 and line 13. A stream containing 141,250 pounds per hour of ethylene dichloride and 125 pounds per hour of ethyl chloride is removed through line 19. The temperature of the liquid ethylene dichloride circulating in line 13 is maintained at 40° C. and the temperature of the liquid exiting column 110 to line 9 is 60° C. The gaseous stream exiting column 110 through line 7 is at a pressure of 49 psig.

The ethylene dichloride rich gas mixture at 60° C. is passed to column 120 which is a 10 feet 6 inch diameter by 8 feet mild steel column containing a 5 foot packed bed of one inch carbon steel raschig rings. The gas stream is contacted countercurrently with a flow of 140,000 pounds per hour of ethylene dichloride which enters the column through line 36 at 40° C. The liquid ethylene dichloride which has contacted the gas mixture in column 120 is then passed to column 110 through line 23. The gas mixture leaving column 120 through line 8 contains:

46,500 pounds per hour $N_2$
1,730 pounds per hour $O_2$
9,100 pounds per hour ethylene dichloride
125 pounds per hour ethyl chloride The gas mixture in line 8 is passed to absorption column 130. Absorption column 130 is a mild steel column, 5 feet, 6 inches in diameter and 40 feet in height containing 30 sieve trays. The gas mixture from line 8 enters the bottom of the column and is countercurrently contacted with 180,000 pounds per hour of a normal nine carbon hydrocarbon solvent which enters the column through line 21 at 40° C. The gas mixture containing only a small quantity of chlorinated hydrocarbons exits column 130 through line 16 and is passed to heat exchanger 40 where it is cooled by heat exchange with the cold gas mixture from dryer 30. The gas stream leaves heat exchanger 40 at −5° C. and condensed liquid is separated from the gas stream in knock-out vessel 70. The liquid collected in vessel 70 is pumped through line 14, pump 80 and line 15 to the bottom of absorber column 130. The vent gas containing only small amounts of ethylene and chlorinated hydrocarbons is removed from the system through line 18. Line 18 contains a back pressure control means to maintain the pressure in vessel 70 at 44 lbs/per square inch gauge.

The gas stream leaving the process through line 18 comprises:

1,730 pounds per hour $O_2$
46,500 pounds per hour $N_2$
28 pounds per hour ethylene
3 pounds per hour ethylene dichloride
5 pounds per hour ethyl chloride
4 pounds per hour hydrocarbon solvent In separator 70 780 pounds/per hour of liquid are collected and pumped to column 130 through line 14, pump 80 and line 15.

The ethylene dichloride rich absorbing liquid in the bottom of column 130 passes from the column through line 22 to heat exchanger 140 where the ethylene dichloride rich solvent is heated to 140° C. by heat exchange with the hot stripped solvent from column 160 and is passed to column 160 through line 37. Since column 130 operates at an elevated pressure and column 160 operates at a lower pressure the pressure difference can be utilized to transfer the ethylene dichloride rich solvent from column 130 to column 160.

Column 160 is a 7 feet 6 inch diameter by 40 feet tall mild steel column containing 30 sieve trays. The ethylene dichloride rich solvent stream containing 180,000 lbs/per hour solvent, 9,100 lbs/per hour ethylene dichloride and 120 lbs/per hour ethyl chloride enters column 160 at the 25th tray from the bottom of the column. The liquid phase flows down through the column and is contacted with vapors supplied by boiling liquid circulating through line 24 reboiler 200 and line 38 at the bottom of column 160. The bottom of the column is maintained at 165° C. The pressure at the top of the column is 5 pounds per square inch gauge. The stripped solvent leaves column 160 through line 23 and pump 210 and passes through line 34 and is cooled by heat interchange with the ethylene dichloride rich solvent from column 130 in heat exchanger 140 and passes through to heat exchanger 150 where the stripped solvent is cooled to 40° C. by heat exchange with cooling water. The stripped solvent then enters column 130 through line 21 at the 30th tray.

The stripped vapor is removed from column 160 through line 25, condensed in heat exchanger 170 and flows through line 26 to reflux accumulator 180. The liquid reflux in accumulator 180 passes through line 27 to pump 190 and through line 31 where it is separated into 39,700 lbs/per hour reflux which enters column 160 through line 28 and 9,250 lbs/per hour product which is removed from the system through line 29.

As will be noted the vent gas which is removed from the system through line 18 contains relatively small amounts of chlorinated hydrocarbons and hydrocarbon solvent and can be vented directly to the atmosphere without adding undue amounts of atmoshperic pollutants to the environment.

Where air pollution considerations are not controlling an alternative embodiment of the present invention can provide an economical embodiment for recovering the ethylene values from the oxychlorination process off-gas. Example 2 is an illustrative embodiment of the process disclosed in FIG. 3.

EXAMPLE 2

Ethylene oxychlorination off-gas at a temperature of 40° C. and 60 psig. containing:
  2,830 pounds per hour ethylene
  1,730 pounds per hour oxygen
  46,500 pounds per hour nitrogen
  430 pounds per hour water
  6,900 pounds per hour ethylene dichloride
  500 pounds per hour ethyl chloride
enters the process through line 1 and is cooled in heat exchanger 10 to −25° C. Hydrogen chloride in the amount of 70 lbs/per hour is added to the gas mixture in line 1 through line 12. The gaseous mixture and condensate flow through line 2 to gas-liquid separator vessel 20 where the liquid is separated from the gaseous material. Gas-liquid separator vessel 20 contains a fiber glass batting type mist eliminator to prevent carry-over of liquid particles from the separator vessel. A liquid mixture of:

250 pounds per hour ethyl chloride
  6,700 pounds per hour ethylene dichloride
  424 pounds per hour water
  70 pounds per hour hydrogen chloride
is removed from vessel 20 through line 3. The cooled gaseous material is removed from vessel 20 through line 4 and is passed to gas dryer vessel 30 which contains a 4 foot 6 inch diameter by 9 feet bed of anhydrous calcium chloride in pellet form. The dried gaseous mixture containing less than about 30 parts per million water (by weight) is passed through heat exchanger 40 where it is warmed by heat exchange with the ethylene deficient gas stream from the top of the contactor-reactor column 100, which is a 10 feet 6 inch diameter by 24 foot column containing an 11 foot packed bed of carbon steel raschig rings in the lower section of the column and a 5 foot packed bed of carbon steel raschig rings in the upper section of the column. The dry gas mixture enters the bottom of column 100 and is contacted countercurrently by 530,000 pounds per hour of ethylene dichloride. The temperature of the liquid ethylene dichloride is maintained between 40° C. and 60° C. by removing the heat of chlorination in heat exchanger 90. The chlorine enters the column through line 19 above the lower section of the packing. The ethylene in the gas stream is reacted with chlorine in the liquid phase and ethylene dichloride is formed. The gas stream then proceeds through the top packed bed where it is contacted with 140,000 pounds per hour of ethylene dichloride, which enters the column through line 22 above the upper packed bed at 40° C. The chlorine which has been stripped from the circulating ethylene dichloride in the lower packed bed is absorbed and reacted with any ethylene which may remain in the gas stream. A gas stream containing 1730 lbs/per hour oxygen, 46,500 lbs/per hour nitrogen, 9,100 lbs/per hour ethylene dichloride, 28 lbs/per hour ethylene and 125 lbs/per hour ethyl chloride, is removed from the top of column 100 through line 7 at a temperature of 40° C. and a pressure of 48 lbs/per square inch gauge and is passed to heat exchanger 40 where the gas is cooled by heat exchange with the cold gas leaving gas dryer 30. The cooled gas stream containing condensed liquid is passed to gas-liquid separator vessel 50 through line 8 where the condensate is separated from the gas. The gas is passed through line 11 to heat exchanger 60 where the gas is cooled to −25° C. and passed through line 13 to gas-liquid separator vessel 70 where the condensate is separated from the uncondensed vent gas. A liquid mixture containing 5,200 lbs/per hour of ethylene dichloride, 25 lbs/per hour ethyl chloride is separated from the gas stream in vessel 50 and passes out of the the system to the crude ethylene dichloride storage through line 9 and 3,700 lbs/per hour ethylene dichloride is separated from the gas stream in separator vessel 70 and passes out of the system through line 14 and is mixed with the ethylene dichloride in line 9. A vent gas stream of 1730 lbs/per hour oxygen, 46,500 lbs/per hour of nitrogen, 200 lbs/per hour of ethylene dichloride, 100 lbs/per hour ethyl chloride and 28 pounds per hour ethylene is passed to the vent system through line 15. Vent line 15 is provided with means for controlling the back pressure in the vessel 70 at 42 lbs. psig. The vent gas which contains a small amount of chlorinated hydrocarbons which can be vented to the atmosphere or can be passed to an incinerator system and burned for recovery of the chlorine values in the form of hydrogen chloride.

EXAMPLE 3

The embodiment of the invention described in FIG. 5 will be illustrated by the following exemplification.

Ethylene oxychlorination off-gas at a temperature of 40° C. and 60 psig containing:
  2,830 pounds per hour ethylene
  1,730 pounds per hour oxygen
  46,500 pounds per hour nitrogen
  430 pounds per hour $H_2O$
  6,900 pounds per hour ethylene dichloride
  500 pounds per hour ethyl chloride
enters the process through line 1 and is cooled in heat exchanger 10 to −25° C. Hydrogen chloride in the amount of 70 pounds per hour is added to the gas mixture in line 1 through line 12. The gaseous mixture and condensate flow through line 2 to gas liquid separator vessel 20 where the liquid is separated from the gaseous material. Gas liquid separator vessel 20 contains a fiber glass batting type mist eliminator to prevent carry-over of liquid particles from the separator vessel. A liquid mixture of:

250 pounds per hour ethyl chloride
6,700 pounds per hour ethylene dichloride
424 pounds per hour water
70 pounds per hour of hydrogen chloride is removed from vessel 20 through line 3. The cooled gaseous material is removed from vessel 20 through line 4 and is passed to heat exchanger 40 where it is warmed to about 25° C. by heat exchange with the ethylene deficient gas stream from the top of contactor-reactor column 100. The gas stream is passed counter-currently to 144,550 pounds per hour of material withdrawn from column 100 through line 18 control valve 44 and line 42.

The further dried gas stream passes from column 240 through line 41 to contactor-reactor 100. Liquid from column 240 passes through line 43 to line 9 and mixes with the condensate from separator 50 and separator 70. The gas stream leaving column 240 is substantially saturated with the chlorinated hydrocarbon materials with which it was countercurrently contacted and contains about 4.2 pounds per hour of water.

The gas stream enters contactor-reactor 100 and is treated in a manner similar to the gas stream entering the contactor-reactor 100 as described in Example 2.

Contacting the gas stream with the ethylene dichloride in contacting drying column 240 reduces the amount of water entering contactor-reactor 100 from about 6 pounds an hour to about 4.2 pounds per hour. The substantial reduction in the amount of water entering the contactor-reactor aids in maintaining the liquid at less than about 50 parts per million water. The ethylene dichloride in the gas stream is recovered in a manner described in Example 2.

The process has the advantage in that the process equipment which is utilized to carry-out the process after dryer 30 can be constructed of mild steel equipment. The use of mild steel equipment presents a capital savings in equipment cost over the corrosion resistant equipment which is required to carry-out the chlorination where a wet oxychlorination off-gas stream is chlorinated.

The process of the present invention has the advantage that the chlorination of ethylene in the liquid phase at relatively low temperatures produces a high yield of the desired ethylene dichloride product without side reactions to undesirable by-products. The vapor phase chlorination process of the prior art for recovering ethylene values from oxychlorination off-gases chlorinate a wet gas stream over a catalyst at an elevated temperature (200° C.) and produce reaction products containing oxygen and hydroxy moieties which must be separated from the product ethylene dichloride. The oxygen and hydroxy containing compounds are usually separated from the ethylene dichloride product by washing with water or dilute hydroxide. The waste wash solution presents a source of water pollution due to the high chemical oxygen demand of these materials in the waste water stream.

The process of the present invention can be successfully operated as long as the reactants are kept relatively moisture free. It is necessary that the ethylene dichloride liquid in the contactor-reactor be maintained below about 50 parts per million and preferably below about 45 parts per million by weight of water. In this range the reaction is rapid, the corrosion rates are relatively low and mild steel equipment can be successfully utilized in the process.

What is claimed is:

1. In a process for preparing ethylene dichloride by oxychlorinating ethylene in which ethylene, hydrogen chloride and an oxygen containing gas are reacted in the presence of an oxychlorination catalyst and where unreacted ethylene values are present in the oxychlorination off-gas; the improvement which comprises recovering the unreacted ethylene values in the oxychlorination process off-gas by the steps of:
   a. cooling the off-gas to condense at least part of the water in the off-gas to form a condensed phase and a gaseous phase;
   b. separating the condensed phase from the gaseous phase thereby providing a partially dried gaseous phase;
   c. contacting the partially dried gaseous phase with ethylene dichloride to further reduce the water content of the partially dried gaseous phase and separating the gaseous phase from the ethylene dichloride;
   d. reacting the ethylene in the gaseous phase from step c) with chlorine in the presence of a non-reactive liquid to form ethylene dichloride; and
   e. recovering the ethylene dichloride; the water content of said off-gas being reduced by said cooling, separating and contacting steps to a level such that the water content of the non-reactive liquid is maintained below about 50 parts per million by weight.

2. The ethylene oxychlorination process of claim 1 wherein the non-reactive liquid is ethylene dichloride.

3. The process of claim 1 wherein the ethylene dichloride is recovered by cooling the gaseous phase, after reaction with chlorine in the presence of liquid ethylene dichloride, to form a liquid phase containing ethylene dichloride and separating the liquid from the gaseous phase.

4. The process of claim 1 which comprises;
   a. cooling the off-gas to a temperature between 5° and −35° C. at a pressure between about 1 and 20 atmospheres to form a condensed phase and a gaseous phase;
   b. separating the condensed phase from the gaseous phase thereby providing a partially dried gaseous phase;
   c. contacting the partially dried gaseous phase with ethylene dichloride and separating the gaseous phase from the ethylene dichloride;
   d. passing the gaseous phase from step c) to a contactor-reactor zone wherein the ethylene in the gaseous phase is reacted with chlorine at a temperature between about 35° and 85° C. in the presence of a non-reactive liquid to form ethylene dichloride; and
   e. recovering the ethylene dichloride leaving the contactor-reactor zone.

5. The process of claim 4 wherein the ethylene dichloride is recovered from the gas stream leaving contactor-reactor zone by absorption in a hydrocarbon solvent at an elevated pressure.

6. The process of claim 4 wherein the ethylene dichloride is recovered from the gas stream leaving contactor-reactor zone by cooling the gas stream leaving the contactor-zone to condense ethylene dichloride and separating the condensate from the cooled gas stream leaving the contactor-reactor zone.

* * * * *